United States Patent
Kim et al.

(10) Patent No.: US 8,683,712 B2
(45) Date of Patent: Apr. 1, 2014

(54) LYOPHILIZING TRAY EMPLOYING REAGENT CARTRIDGE, LYOPHILIZING SYSTEM EMPLOYING THE SAME, AND METHOD OF PREPARING LYOPHILIZED REAGENT

(75) Inventors: Do-gyoon Kim, Yongin-si (KR);
Han-sang Kim, Osan-si (KR);
Jung-nam Lee, Incheon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 508 days.

(21) Appl. No.: 12/574,206

(22) Filed: Oct. 6, 2009

(65) Prior Publication Data
US 2010/0101106 A1 Apr. 29, 2010

(30) Foreign Application Priority Data
Oct. 23, 2008 (KR) ........................ 10-2008-0104268

(51) Int. Cl.
*F26B 11/18* (2006.01)
*F26B 5/06* (2006.01)
*A47G 29/00* (2006.01)

(52) U.S. Cl.
USPC ............... 34/193; 34/194; 34/296; 211/71.01

(58) Field of Classification Search
USPC ............ 34/92, 103, 192–194, 296, 284, 286, 34/287, 203, 297, 289; 222/526, 547, 549, 222/539, 540; 220/312, 345.1, 507; 211/126.1, 126.5, 94.01, 71.01; 70/453, 454; 206/557, 718, 561, 564, 206/499, 379; 249/117, 142
See application file for complete search history.

(56) References Cited

U.S. PATENT DOCUMENTS

| 3,286,365 | A | 11/1966 | Hackenberg |
| 3,647,105 | A * | 3/1972 | Keeslar ........................ 220/23.4 |
| 7,695,230 | B2 * | 4/2010 | Selch ............................ 414/180 |
| 2001/0001348 | A1 * | 5/2001 | Wisniewski .................... 34/284 |
| 2006/0263179 | A1 | 11/2006 | Selch |

OTHER PUBLICATIONS

Communication dated Mar. 25, 2013, issued by the State Intellectual Property Office of P.R. China in counterpart Chinese Application No. 200910180735.6.

* cited by examiner

*Primary Examiner* — Kenneth Rinehart
*Assistant Examiner* — John McCormack
(74) *Attorney, Agent, or Firm* — Sughrue Mion, PLLC

(57) ABSTRACT

A method of manufacturing a lyophilized reagent, including mounting a plurality of reagent cartridges in which a liquid reagent is loaded in a tray including one or more tunnel-shaped first rails having opened end portions in a lengthwise direction and an opening formed in the top of the one or more first rails; closing the opened end portions, placing the tray in a lyophilizer and lyophilizing the liquid reagent according to a lyophilizing program.

27 Claims, 9 Drawing Sheets

LYOPHILIZING TRAY EMPLOYING REAGENT CARTRIDGE, LYOPHILIZING SYSTEM EMPLOYING THE SAME, AND METHOD OF PREPARING LYOPHILIZED REAGENT

CROSS-REFERENCE TO RELATED APPLICATIONS

This application claims priority from Korean Patent Application No. 10-2008-0104268, filed on Oct. 23, 2008, in the Korean Intellectual Property Office, the disclosure of which is incorporated herein in its entirety by reference.

BACKGROUND

1. Field

One or more embodiments relate to a lyophilizing tray employing a reagent cartridge containing a liquid reagent for lyophilization, a lyophilizing system employing the lyophilizing tray, and a method of preparing a lyophilizing reagent.

2. Description of the Related Art

Various methods of analyzing a sample have been developed to, for example, monitor environments, examine food, or diagnose the medical condition of a patient. However, these methods require many manual operations and various devices. To perform an examination according to a predetermined protocol, those skilled in the manual operations repeatedly perform various processes including loading of a reagent, mixing, isolating and transporting, reacting, and centrifuging. However, such manual, repeated processes, may result in erroneous results due to "human error."

To perform examinations quickly, skilled clinical pathologists are needed. However, it is difficult for even a skilled clinical pathologist to perform various examinations at the same time. Even more seriously, rapid examination results are necessary for immediate treatment of emergency patients. Accordingly, there is a need to develop various types of equipment enabling the simultaneous, rapid and precise performance of pathological examinations for given circumstances.

Related art pathological examinations are performed with large and expensive pieces of automated equipment and a relatively large amount of a sample, such as blood. Moreover, results of pathological examinations may only be available from two days (at a minimum) to two weeks after receiving the blood sample from a patient.

To address the above described problems, small and automated pieces of equipment for analyzing a sample taken from one or, if needed, a small number of patients over a short time period have been developed. An example of such a system involves the use of a microfluidic device whereby blood is loaded into a disc-shaped microfluidic device and the disc-shaped microfluidic device is rotated to isolate serum from the blood due to the centrifugal force. The isolated serum is mixed with a predetermined amount of a diluent and the mixture then flows to a plurality of reaction chambers in the disc-shaped microfluidic device. Next, the reaction chambers are filled with reagents prior to allowing the mixture to flow therein. Regents used may differ according to of the goal of the blood tests. When the serum reacts with different reagents, predetermined colors may appear. The change in color is used to perform blood analysis.

SUMMARY

One or more embodiments include a lyophilizing tray employing a plurality of reagent cartridges containing a liquid reagent for lyophilization and a lyophilizing system employing the lyophilizing tray.

One or more embodiments include a method of preparing a lyophilizing reagent in order to lyophilize a liquid reagent contained in a plurality of reagent cartridges by using a lyophilizing tray.

According to an aspect of one or more embodiments, there is provided a manufacturing a lyophilized reagent, the method including: preparing a tray including one or more tunnel-shaped first rails having opened end portions opened in a lengthwise direction and an opening formed in the top of the one or more first rails; loading a liquid reagent into a plurality of reagent cartridges; mounting the plurality of reagent cartridges into which the liquid reagent is loaded in the one or more first rails of the tray via the opened end portions, and closing the opened end portions; putting the tray in a lyophilizer and lyophilizing the liquid reagent according to a lyophilizing program; and taking the tray out of the lyophilizer.

The loading of the liquid reagent may include: preparing a loading tray including one or more second rails having opened upper portions and opened end portions in a lengthwise direction; mounting the plurality of reagent cartridges in the one or more second rails of the loading tray via the opened end portions; and loading a precise amount of the liquid reagent on the plurality of reagent cartridges via the opened upper portions of the loading tray.

The loading tray and the tray may be arranged so that the end portions of the one or more first and second rails face each other, and the plurality of reagent cartridges mounted in the one or more second rails are pushed toward the one or more first rails and are moved toward the one or more second rails.

After lyophilization is completed, the opening may be closed by using a stopper, the plurality of reagent cartridges may be stored in the sealed tray, and the tray is took out of the lyophilizer.

An inert gas may be injected into the tray and the opening is closed.

The lyophilizer may include a plurality of shelves on which the tray is disposed, wherein the tray is disposed on the plurality of shelves when the stopper is coupled to the opening so as to allow a flow of a gas through the opening.

The plurality of shelves may be moved to push the stopper and close the opening.

According to another aspect of one or more embodiments, there is provided a lyophilizing tray including: one or more tunnel-shaped rails having opened end portions in a lengthwise direction and in which a plurality of reagent cartridges are to be mounted; one or more openings formed in the top of the one or more rails; a first stopper closing the one or more openings; and a second stopper closing the opened end portions.

A space may be formed in the top of the one or more rails so as to allow a gas to flow.

The first stopper may include a first position used to allow input and output of a gas via the one or more openings and a second position used to tightly close the one or more openings when the first stopper is coupled to the one or more openings.

A vent may be formed in the first stopper so as to allow a flow of gas in the first position.

According to another aspect of one or more embodiments, there is provided a lyophilizing system including: a loading tray including one or more second rails having opened upper portions and opened end portions in a lengthwise direction and in which a plurality of reagent cartridges are to be mounted; a loader loading a precise amount of a liquid reagent on the plurality of reagent cartridges mounted in the loading tray; a lyophilizing tray including one or more tunnel-shaped rails having opened end portions in a lengthwise direction and in which a plurality of reagent cartridges containing the liquid reagent are to be mounted; and a lyophilizer storing the lyophilizing tray and lyophilizing the liquid reagent.

One or more openings may be formed in the top of the one or more first rails so as to connect the inside and outside of the lyophilizing tray.

A space may be formed in the top of the one or more first rails so as to allow a flow of a gas.

The lyophilizing system may further comprise: a first stopper closing the one or more openings; and a second stopper closing the end portions of the one or more second rails.

The first stopper may include a first position used to allow input and output of a gas via the one or more openings and a second position used to tightly close the one or more openings when the first stopper is coupled to the one or more openings.

A vent may be formed in the first stopper so as to allow a flow of gas in the first position.

The lyophilizing tray may be stored in the lyophilizer where the first stopper is coupled to the one or more openings so that the first stopper is in the first position, wherein the lyophilizer includes one or more shelves on which the lyophilizing tray is disposed, a fixing plate positioned on the one or more shelves, and an actuator moving the one or more shelves toward the fixing plate, wherein, after lyophilization is completed, the one or more shelves are moved toward the fixing plate so that the first stopper is moved toward the second position and the one or more openings are closed.

BRIEF DESCRIPTION OF THE DRAWINGS

The above and/or other aspects will become apparent and more readily appreciated from the following description of the exemplary embodiments, taken in conjunction with the accompanying drawings of which.

DETAILED DESCRIPTION

Figure 1:
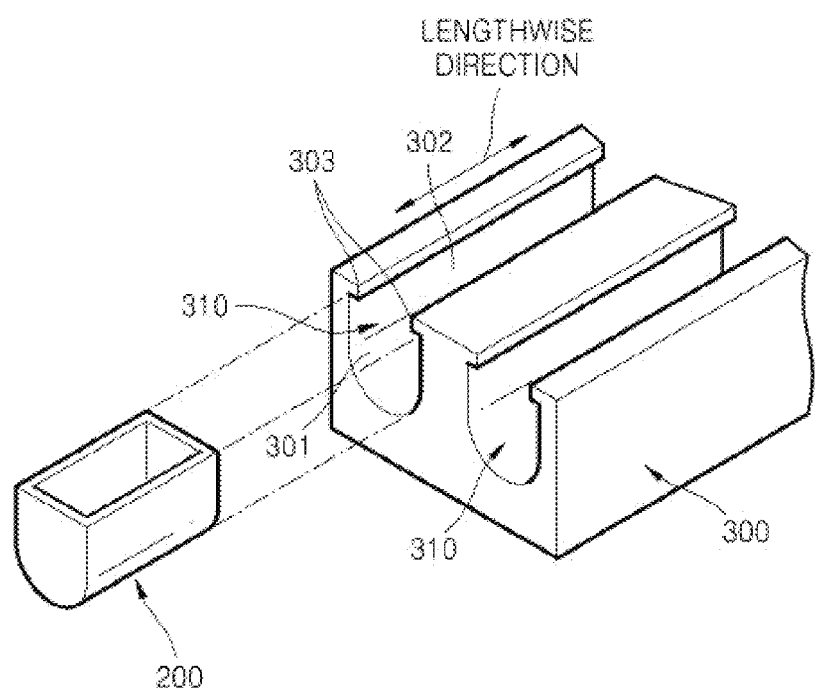
FIG. 1 is a perspective view of a loading tray according to an exemplary embodiment.

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

FIG. 1 is a perspective view of a loading tray 300 according to an exemplary embodiment of the inventive concept. Referring to FIG. 1, the loading tray 300 comprises two second rails 310 which are tunnel-shaped and extend in a lengthwise direction. The second rails 310 have opened upper portions 302 which are open in a vertical direction and opened end portions 301 which are open in the lengthwise direction. Although the loading tray 300 of the present inventive concept comprises the two second rails 310, the inventive concept is not limited thereto such that the loading tray 300 may comprise one second rail or more than two second rails. A plurality of reagent cartridges 200 are mounted in the second rails 310 of the loading tray 300 via the opened end portions 301. A plurality of detachment preventive projections 303 are formed in the second rails 310 in order to prevent the reagent cartridge 200 from being detached through the upper potions 302.

Figure 2:
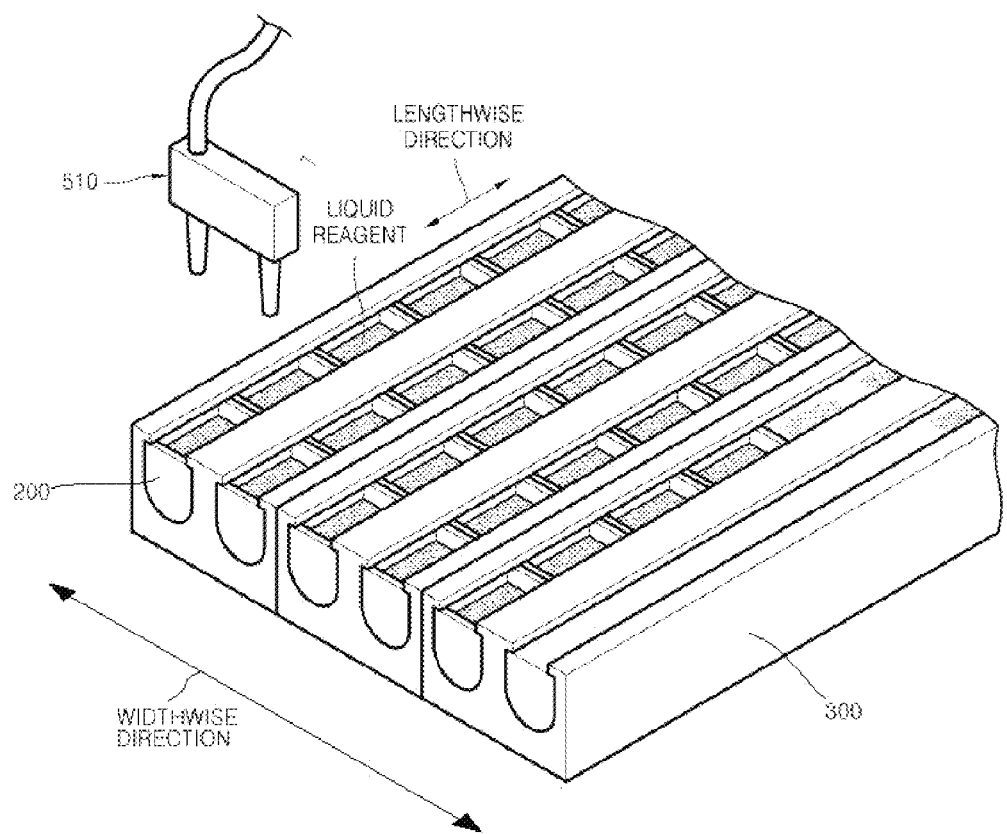
FIG. 2 is a perspective view for explaining a process of loading a liquid reagent on a plurality of reagent cartridges according to an exemplary embodiment.

FIG. 2 is a perspective view for explaining a process of loading a liquid reagent on the reagent cartridges 200 mounted in a plurality of loading trays 300 according to an exemplary embodiment of the inventive concept. Referring to FIG. 2, a loader 510 is connected to a reagent tank (not shown) in which the liquid reagent is stored. The loading trays 300 may be arranged horizontally. A precise amount of the liquid reagent is loaded in each of the reagent cartridges 200 through the upper portions 302 of the loading trays 300 by moving the loader 510 in the lengthwise direction and a horizontal direction. The reagent cartridges 200 are mounted in the second rails 310 of the loading trays 300, thereby effectively loading a very small and precise amount of liquid reagent. In more detail, since the reagent cartridges 200 have uniform sizes, it is very easy to locate the reagent cartridges 200 arranged in the second rails 310. Thus, it is possible to quickly and precisely load the liquid reagent by using the automated loader 510 such as a loading robot, etc.

Figure 3:
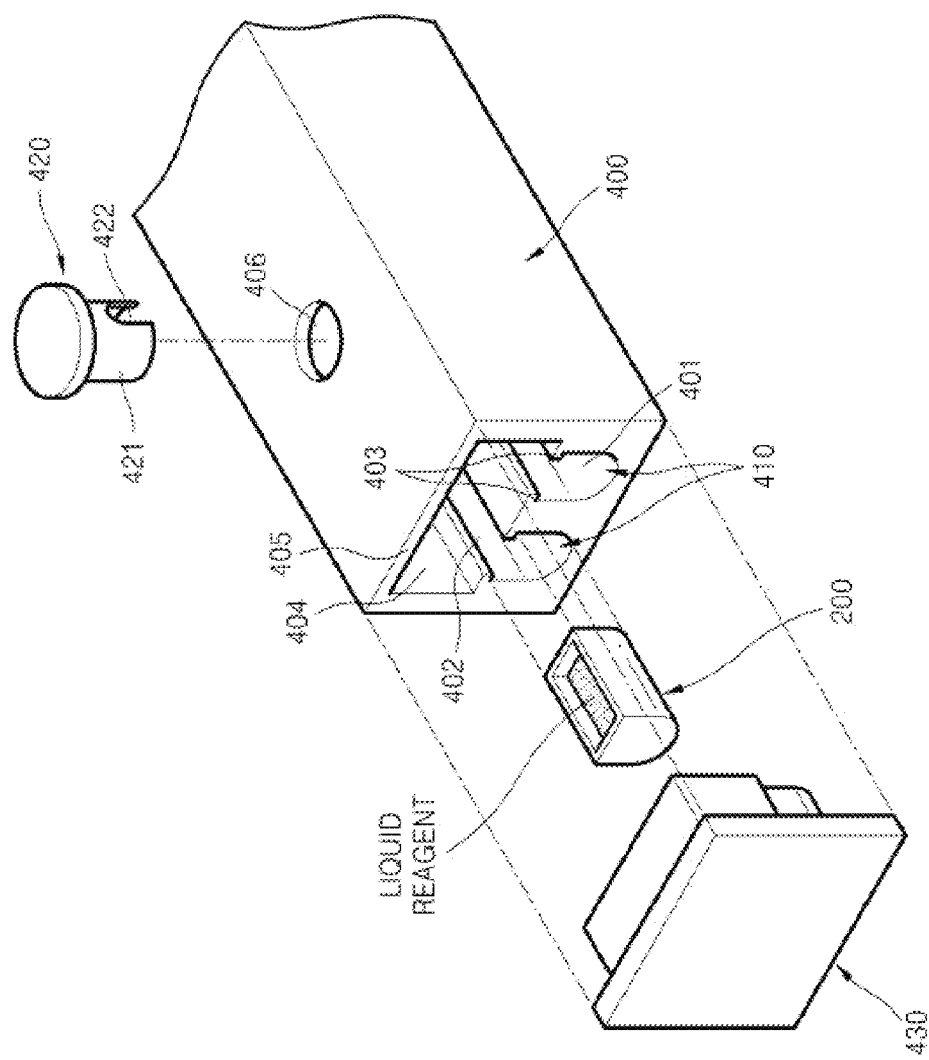
FIG. 3 is a perspective view of a lyophilizing tray according to an exemplary embodiment.

Next, the reagent cartridges 200 in which the liquid reagent is loaded are carried from the loading trays 300 to a lyophilizing tray 400. FIG. 3 is a perspective view of the lyophilizing tray 400 according to an exemplary embodiment of the inventive concept. Referring to FIG. 3, the lyophilizing tray 400 comprises two first rails 410, an interior space 404 provided above the first rails 410, and an upper wall 405. The first rails 410 are tunnel-shaped and extend in a lengthwise direction of the lyophilizing tray 400. End portions 401 of the first rails 410 are open in the lengthwise direction. Upper portions 402 of the first rails are open in a vertical direction to the space 404 which is closed by an upper wall 405. The first rails 410 include detachment preventive projections 403 to prevent the reagent cartridges 200 from being detached through the upper portions 402. Although the lyophilizing tray 400 comprises two first rails 410 in the present exemplary embodiment, the inventive concept is not limited thereto such that the lyophilizing tray 400 may comprise one first rail or more than two first rails. An opening 406 is formed in the upper wall 405 so as to connect the lyophilizing tray 400 to the outside. A plurality of openings 406 may be formed in the upper wall 405. A first stopper 420 is used to close the opening 406. The first stopper 420 may comprise a column portion 421 inserted into the opening 406. The column portion 421 may be hollow. A vent 422 may be formed in the column portion 421. A second stopper 430 is inserted in the lengthwise direction to close the end portions 401 in the widthwise direction of the first rails 410. Although not shown, a complementary type stacked structure may be formed on the upper and lower exterior sides of the lyophilizing tray 400 so that a plurality of lyophilizing trays 400 stacked in up and down directions can be stably coupled to each other so as to facilitate maintenance or carrying of a lyophilized reagent.

The first stopper 420 is movable between in two positions, i.e., a first position to allow input and output of a gas via the opening 406, and a second position to tightly close the opening 406. In more detail, referring to FIG. 4A, the first stopper 420 is partially inserted in the opening 406 so that vent 422 is exposed to the exterior, thereby connecting the inside and outside of the lyophilizing tray 400 via the vent 422. Thus, the gas can be injected into and discharged from the lyophilizing tray 400 via the vent 422. Referring to FIG. 4B, the first stopper 420 is fully inserted in the opening 406, thereby closing the opening 406 and preventing the gas from being injected into and discharged from the lyophilizing tray 400.

Figure 5:
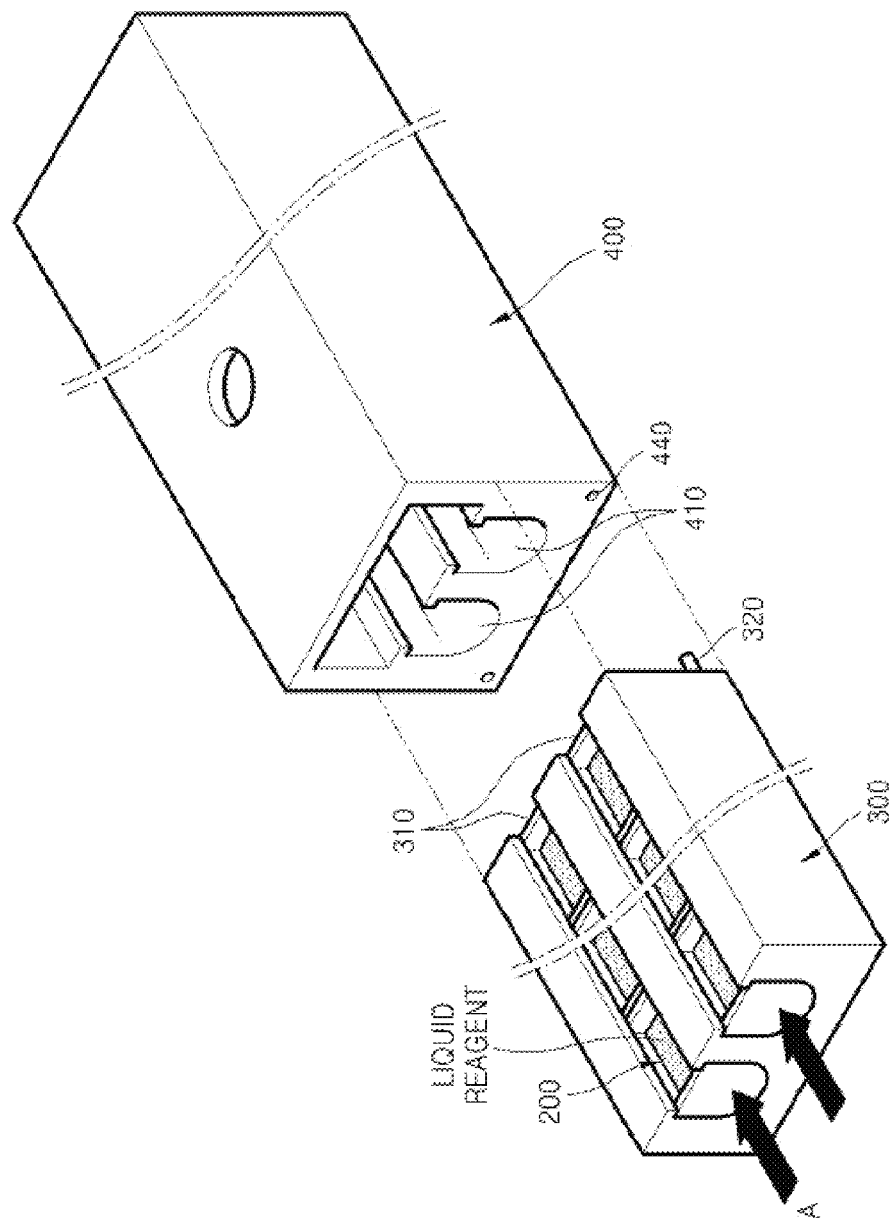
FIG. 5 is a perspective view for explaining a process of carrying a plurality of reagent cartridges in which a liquid reagent is loaded from a plurality of loading trays to a plurality of lyophilizing trays according to an exemplary embodiment.

Referring to FIG. 5, in order to move the reagent cartridges 200 in which the liquid reagent is loaded from the loading trays 300 to the lyophilizing trays 400, the loading trays 300 and the lyophilizing trays 400 are positioned so that the end portions 401 of the first rails 410 face and contact the end portions 301 of the second rails 310 each other. A projection 320 and a hole 440 are formed in the loading trays 300 and the lyophilizing trays 400, respectively, to insert the projection 320 into the hole 440, so that the first and second rails 410 and 310 may face each other in proper alignment. Thereafter, the reagent cartridges 200 inside the second rails 310 are pushed toward the first rails 410 as indicated by an arrow A via the end portions 301 of the loading trays 300. The reagent cartridges 200 are slid along the second rails 310 and are moved inside the first rails 410. After the reagent cartridges 200 are disposed in the first rails 410, the end portions 401 of the lyophilizing trays 400 are closed by inserting the second stopper 430.

Figure 6:
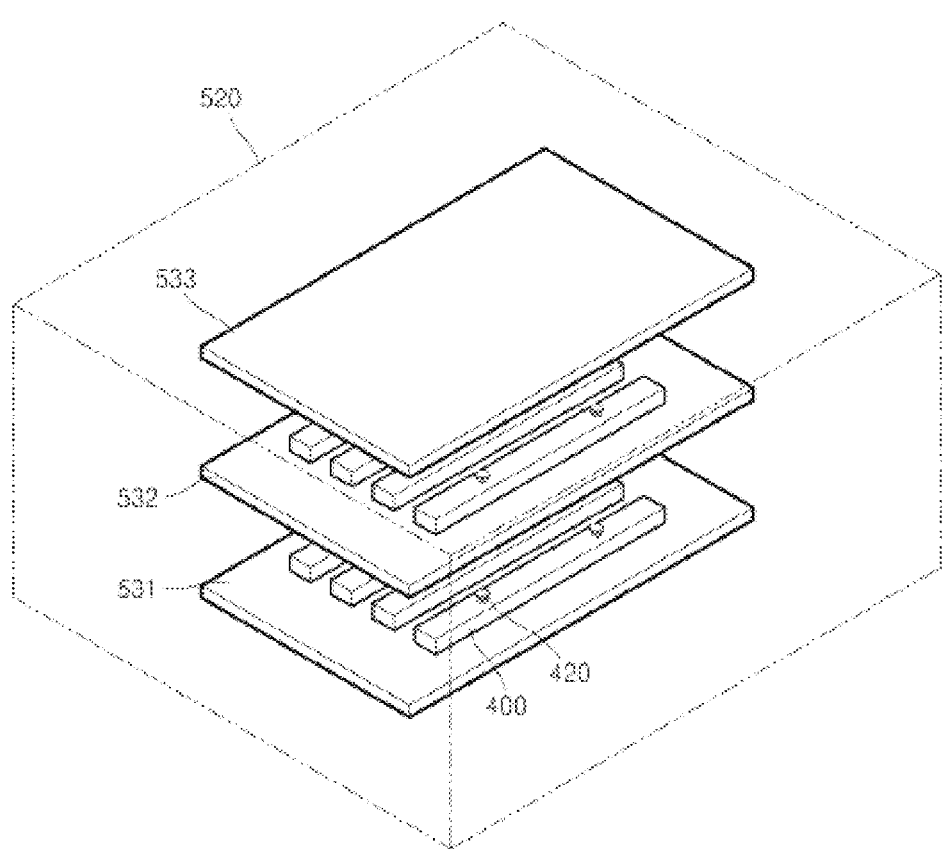
FIG. 6 is a perspective view for explaining a lyophilizing process according to an exemplary embodiment.

A lyophilizing process will now be described with reference to FIG. 6.

Figure 4A:
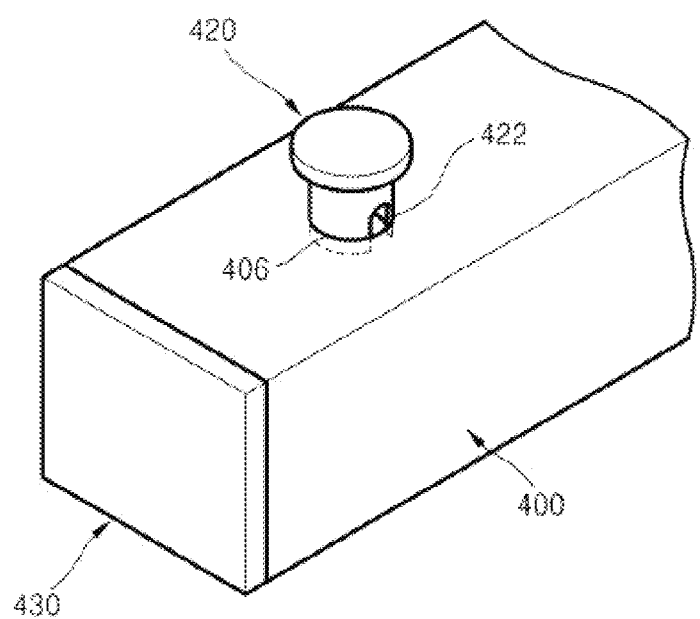
FIG. 4A is a perspective view of a first stopper coupled to an opening of a lyophilizing tray to allow a flow of gas according to an exemplary embodiment.
Figure 4B:
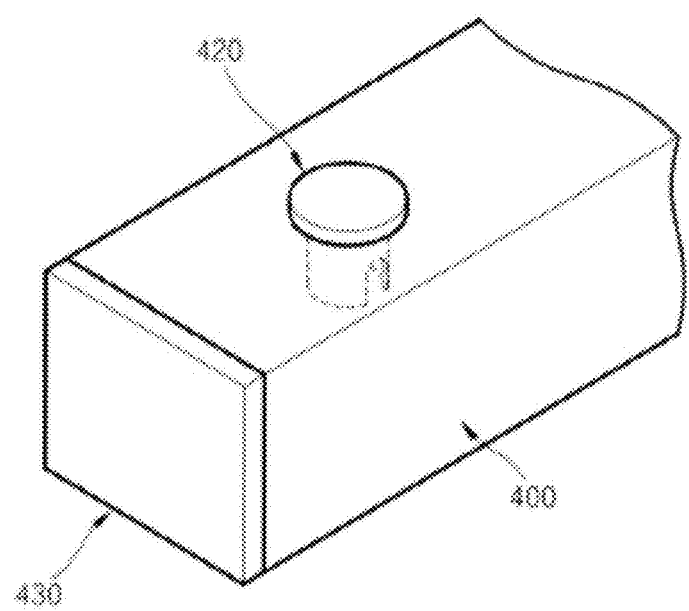
FIG. 4B is a perspective view of the opening of the lyophilizing tray tightly closed by the first stopper according to an exemplary embodiment.

As shown in FIG. 4A, the first stopper 420 is coupled to the opening 406 of the lyophilizing trays 400 so as to allow a gas to be input to and output from the lyophilizing trays 400. The lyophilizing trays 400 are disposed on shelves 531 and 532 of a lyophilizer 520. The lyophilizing process is performed according to a predetermined lyophilizing program. The lyophilizing program performs a freezing process of freezing water included in a liquid reagent and a drying process of removing water of the frozen reagent. In general, the drying process uses a sublimating process whereby frozen water is directly vaporized. However, the entire drying process does not necessarily require sublimation, that is, only a part of the drying process may require sublimation. To perform the sublimating process, the pressure in the drying process may be adjusted to be equal to or lower than the triple point of water (6 mbar or 4.6 Torr). However, it may not be necessary to maintain a predetermined pressure. In the drying process, the temperature may be changed. For example, after the freezing process is completed, the temperature may be gradually increased. The lyophilizing program may appropriately vary according to the amount and type of liquid reagent. In the lyophilizing process, the water vapor separated from the liquid reagent is discharged to the outside of the lyophilizing trays 400 via the opening 406 and the vent 422. The lyophilizing trays 400 include the space 404, so that the water vapor more easily flows inside the lyophilizing trays 400 and is more easily discharged to the outside through the opening 406 and the vent 422.

Figure 7A:
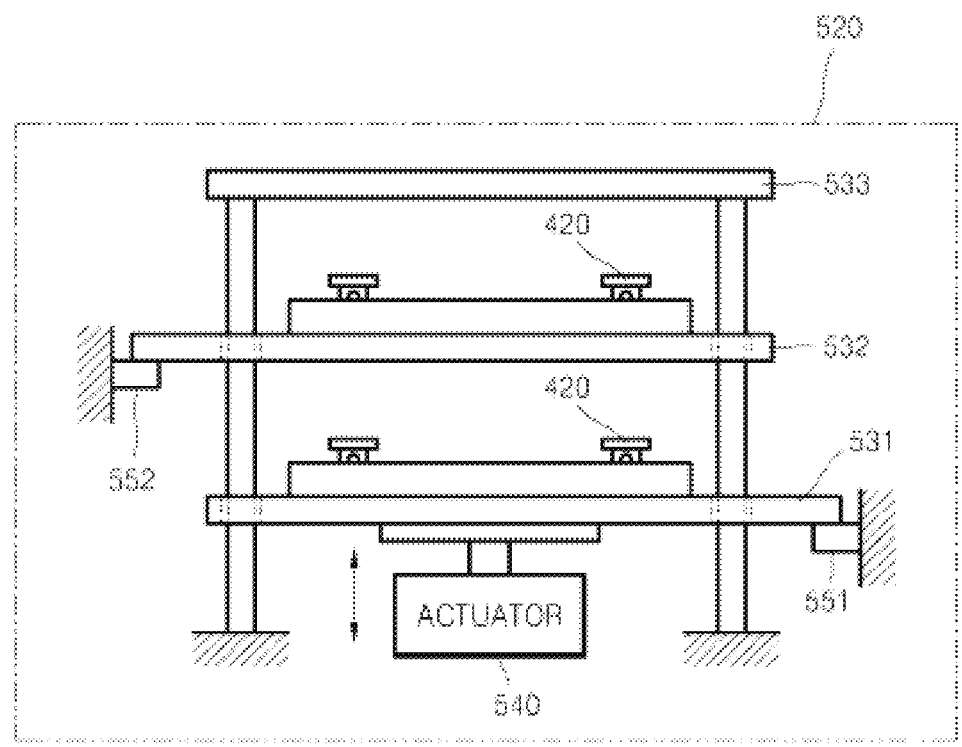
FIGS. 7A and 7B are diagrams of an opening of a lyophilisation tray closed by using a second stopper according to an exemplary embodiment.
Figure 7B:
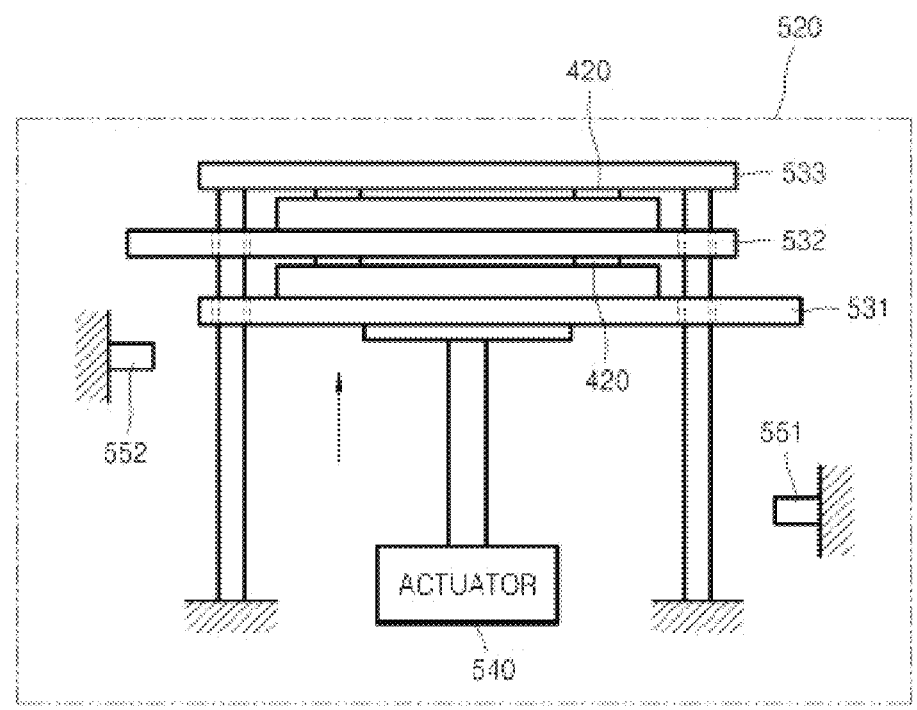

If the lyophilizing process is completed, the opening 406 is closed by fully inserting the first stopper 420 as shown in FIG. 4B before the lyophilizing trays 400 are removed from the lyophilizer 520. The opening 406 may be closed by, for example, by moving the shelves 531 and 532 of the lyophilizer 520. In more detail, referring to FIGS. 7A and 7B, the shelves 531 and 532 of the lyophilizer 520 may be moved up and down by using an actuator 540. After the lyophilizing process is completed, the actuator 540 upwardly pushes the shelf 531 towards the shelf 532 and thus the shelf 531 moves in an upward direction. The first stoppers 420 of the lyophilizing trays 400 positioned above the shelf 531 contact the shelf 532 and thus the shelf 532 moves in an upward direction. When the first stoppers 420 of the lyophilizing trays 400 above the shelf 532 contact a fixing plate 533, if the actuator 540 continues pushing the shelf 531 upward, the first stoppers 420 are pushed downward and thus the opening 460 is tightly closed as shown in FIG. 4B. Thereafter, if the actuator 540 is returned to its original state, the shelves 531 and 532 are moved in a downward direction. The shelf 532 is hung from a position determining unit 552, and the shelf 531 is hung from a position determining unit 551, so that the shelves 531 and 532 are restored to their original states as shown in FIG. 7A.

The lyophilizing trays 400 are then taken out of the lyophilizer 520. The lyophilizing trays 400 are refrigerated so as to maintain stability of the liquid reagent. The lyophilizing trays 400 are carried in a refrigerated state. When a microfluidic device is manufactured, the reagent cartridges 200 removed one by one from the lyophilizing trays 400 by opening the second stoppers 430 of the lyophilizing trays 400 and are mounted on the reaction chambers 70. For example, although not shown, each of the first rails 410 of the lyophilizing tray 400 may include opened end portions 401 opposite ends of the first rails 410 in the lengthwise direction, and two second stoppers 430 may be inserted in the opened end portions 401 to close the end portions 401 prior to lyophilization. In this case, after lyophilization, the reagent cartridges 200 may be removed from the lyophilizing tray 400 by removing the two second stoppers 430 from the opened end portions 401, and pushing the reagent cartridges 200 mounted in the first rails 410 from one of the opened end portions 401 so the reagent cartridges slide out of the other one of the opened end portions 401.

In the lyophilizing process, the lyophilizer 520 remains in a near-vacuum state. Therefore, as described above, if the opening 406 of the lyophilizing trays 400 is closed in the lyophilizer 520, the lyophilizing trays 400 are sealed in the near-vacuum state, thereby facilitating stabilization of a reagent. An inert gas such as nitrogen may be injected into the lyophilizing trays 400 before the opening 406 is closed.

As described above, according to the exemplary embodiments, the lyophilizing method can effectively deal with a very small amount of reagent, and produce a great amount of reagents having constant quality.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

What is claimed is:

1. A lyophilizing tray comprising:
   at least one rail, wherein the rail is a tunnel-shaped through-hole extending in the lengthwise direction of the tray, and the rail includes an opened end portion which is open in a lengthwise direction of the tray and in which a plurality of reagent cartridges are to be mounted, an opened upper portion which is open in a vertical direction and detachment preventative projections configured to directly engage the plurality of reagent cartridges and prevent the reagent cartridges from being detached through the opened upper portion;
an upper wall disposed above the at least one rail and having at least one opening formed therein;
a first stopper which is removably inserted in the opening of the upper wall to close the opening; and
a second stopper which is removably inserted in the end portion of the rail to close the end portion.

2. The lyophilizing tray of claim 1, wherein a space is formed between the upper portion of the rail and the upper wall to allow a gas to flow.

3. The lyophilizing tray of claim 1, wherein the first stopper is movable between a first position which allows input and output of a gas via the opening, and a second position which fully closes the opening.

4. The lyophilizing tray of claim 3, wherein the first stopper includes a vent to allow a flow of gas in the first position.

5. The lyophilizing tray of claim 2, wherein the detachment preventive projections are configured to engage and project over a top surface of the reagent cartridges to prevent the reagent cartridges from being detached through the upper portion.

6. A lyophilizing system comprising:
a lyophilizing tray comprising at least one first rail, wherein the first rail is a tunnel-shaped through-hole extending in a lengthwise direction of the lyophilizing tray, and the first rail includes an opened end portion which is open in a lengthwise direction of the lyophilizing tray, an opened upper portion which is open in a vertical direction, and detachment preventative projections configured to directly engage a plurality of reagent cartridges and prevent the reagent cartridges from being detached through the opened upper portion;
a loading tray comprising at least one second rail, wherein the second rail is a tunnel-shaped through-hole extending in a lengthwise direction of the loading tray, and the second rail includes an opened upper portion and an opened end portion which is open in a lengthwise direction of the loading tray and in which the plurality of reagent cartridges are mounted, and detachment preventative projections configured to directly engage the plurality of reagent cartridges and prevent the reagent cartridges from being detached through the opened upper portion;
a loader which loads an amount of a liquid reagent in the plurality of reagent cartridges mounted in the second rail of the loading tray; and
a lyophilizer in which the lyophilizing tray is stored, wherein the lyophilizer lyophilizes the liquid reagent loaded in the plurality of reagent cartridges.

7. The lyophilizing system of claim 6, wherein the lyophilizing tray further comprises an upper wall which is disposed above the first rail and has at least one opening formed therein.

8. The lyophilizing system of claim 7, wherein a space is formed between the opened upper portion of the first rail and the upper wall of the lyophilizing tray so as to allow a flow of a gas.

9. The lyophilizing system of claim 7, further comprising:
a first stopper which is removably inserted in the opening of the upper wall of the lyophilizing tray to close the opening; and
a second stopper which is removably inserted in the end portion of the first rail of the lyophilizing tray to close the end portion.

10. The lyophilizing system of claim 9, wherein the first stopper is movable between a first position which allows input and output of a gas via the opening, and a second position which fully closes the opening.

11. The lyophilizing system of claim 10, wherein the lyophilizing tray is stored in the lyophilizer in a state in which the first stopper is in the first position,
wherein the lyophilizer comprises at least one shelf on which the lyophilizing tray is disposed, a fixing plate which is disposed above the shelf, and an actuator which moves the shelf toward the fixing plate,
wherein, after lyophilization is completed by the lyophilizer, the shelf is moved toward the fixing plate so that the first stopper is moved to the second position to close the opening.

12. The lyophilizing system of claim 6, wherein the detachment preventive projections are configured to engage and project over a top surface of the reagent cartridges to prevent the reagent cartridges from being detached through the upper portion.

13. A method of manufacturing a lyophilized reagent, the method comprising:
mounting a plurality of reagent cartridges into rails of a loading tray, wherein the rails are tunnel-shaped through-holes extending in a lengthwise direction of the loading tray, and the rails include open ends which are open in a lengthwise direction of the rails, an opened upper portion which is open in a vertical direction, and detachment preventative projections configured to directly engage the plurality of reagent cartridges and prevent the reagent cartridges from being detached through the opened upper portion;
loading a liquid reagent into the plurality of reagent cartridges mounted in the rails of the loading tray;
aligning the open ends of the rails of the loading tray with open ends of rails of a lyophilizing tray, wherein the rails of the lyophilizing tray are tunnel-shaped through-holes extending in a lengthwise direction of the lyophilizing tray, and moving the plurality of reagent cartridges into which the liquid reagent is loaded from the rails of the loading tray into the rails of the lyophilizing tray via the opened end portions of the rails of the loading tray and the lyophilizing tray;
closing the open ends of the rails of the lyophilizing tray and placing the lyophilizing tray in a lyophilizer; and
lyophilizing the liquid reagent using the lyophilizer.

14. The lyophilizing tray of claim 1, wherein the first rail has an inverted arched cross-section.

15. The lyophilizing system of claim 6, wherein the first rail and second rail have an inverted arched cross-section.

16. The method of claim 13, wherein the detachment preventive projections are configured to engage and project over a top surface of the reagent cartridges to prevent the reagent cartridges from being detached through the upper portion.

17. The method of claim 13, wherein the rails of the loading tray and the rails of the lyophilizing tray have inverted arched cross-section.

18. A method of manufacturing a lyophilized reagent, the method comprising:
preparing a tray comprising at least one first rail, and an upper wall disposed above the first rail and including an opening formed therein, wherein the first rail is a tunnel-shaped through-hole extending in a lengthwise direction of the tray, and the first rail includes an opened end portion which is open in the lengthwise direction of the tray, an opened upper portion which is open in a vertical direction, and detachment preventative projections configured to directly engage a plurality of reagent cartridges and prevent the reagent cartridges from being detached through the opened upper portion;

loading a liquid reagent into the plurality of reagent cartridges;

mounting the plurality of reagent cartridges into which the liquid reagent is loaded in the first rail of the tray via the opened end portion of the first rail, and closing the opened end portion;

placing the tray in a lyophilizer and lyophilizing the liquid reagent according to a lyophilizing program; and removing the tray from the lyophilizer.

19. The method of claim 18, wherein the loading the liquid reagent comprises:

preparing a loading tray comprising at least one second rail, wherein the second rail is a tunnel-shaped throughhole extending in a lengthwise direction of the loading tray and includes an opened upper portion and an opened end portion which is open in a lengthwise direction;

mounting the plurality of reagent cartridges in the second rail of the loading tray via the opened end portion of the second rail; and loading an amount of the liquid reagent in the plurality of reagent cartridges mounted in the second rail of the loading tray through the opened upper portion of the second rail.

20. The method of claim 19, wherein the mounting the plurality of reagent cartridges into which the liquid reagent is loaded in the first rail of the tray comprises:

arranging the loading tray and the tray so that the end portion of the first rail of the tray and the end portion of the second rail of the loading tray contact each other; and pushing the plurality of reagent cartridges mounted in the second rail toward the first rail so that the plurality of reagent cartridges are moved from the second rail into the first rail.

21. The method of claim 18, further comprising, after lyophilization is completed, closing the opening of the upper wall of the tray by inserting a stopper in the opening so that the tray is sealed with the plurality of reagent cartridges stored therein, and removing the tray from the lyophilizer.

22. The method of claim 21, further comprising, before the closing the opening of the upper wall of the tray, injecting an inert gas into the tray.

23. The method of claim 21, wherein the lyophilizer comprises a plurality of shelves, and wherein the placing the tray in the lyophilizer comprises placing the tray on one of the plurality of shelves when the stopper is coupled to the opening so as to allow a flow of a gas through the opening.

24. The method of claim 23, wherein the plurality of shelves are moved to push down the stopper to fully close the opening.

25. The lyophilizing system of claim 24, wherein the first stopper includes a vent to allow a flow of gas in the first position.

26. The method of claim 18, wherein the detachment preventive projections are configured to engage and project over a top surface of the reagent cartridges to prevent the reagent cartridges from being detached through the upper portion.

27. The method of claim 18, wherein the first rail has an inverted arched cross-section.

* * * * *